(12) United States Patent
Tang et al.

(10) Patent No.: US 11,680,062 B2
(45) Date of Patent: Jun. 20, 2023

(54) 3,4-METHYLENEDIOXYPHENYLIMIDAZO-LYLETHANONEXIME ETHER DERIVATIVE, PREPARATION METHOD AND USE THEREOF, AND DRUG FOR THE TREATMENT OF ALZHEIMER'S DISEASE

(71) Applicant: NORTHWEST A&F UNIVERSITY, Xianyang (CN)

(72) Inventors: Jiangjiang Tang, Xianyang (CN); Zhaoyuan Bian, Xianyang (CN); Lanfang Huang, Xianyang (CN); Bo Ren, Xianyang (CN); Ping Xiang, Xianyang (CN); Jinming Gao, Xianyang (CN)

(73) Assignee: NORTHWEST A & F UNIVERSITY, Xianyang (CN)

( * ) Notice: Subject to any disclaimer, the term of this patent is extended or adjusted under 35 U.S.C. 154(b) by 0 days.

(21) Appl. No.: 17/670,911

(22) Filed: Feb. 14, 2022

(65) Prior Publication Data
US 2023/0159503 A1    May 25, 2023

(30) Foreign Application Priority Data
Nov. 25, 2021 (CN) .......................... 202111412170.7

(51) Int. Cl.
C07D 405/06    (2006.01)
A61P 25/28    (2006.01)

(52) U.S. Cl.
CPC ............ *C07D 405/06* (2013.01); *A61P 25/28* (2018.01)

(58) Field of Classification Search
CPC .............................. C07D 405/06; A61P 25/28
See application file for complete search history.

(56) References Cited

FOREIGN PATENT DOCUMENTS

CN    113429398    *    9/2021

* cited by examiner

*Primary Examiner* — D Margaret M Seaman
(74) *Attorney, Agent, or Firm* — Troutman Pepper Hamilton Sanders LLP (Rochester)

(57) ABSTRACT

Disclosed are 3,4-methylenedioxyphenylimidazolyletha-nonexime ether derivatives, a preparation method and use thereof, and a drug for the treatment of Alzheimer's disease, which relates to the technical field of preparation of acetophenone oxime ether compounds. The (Z)-3,4-methylenedioxyphenylimidazolylethanonexime ether derivatives provided by the present disclosure show a significant effect on the inhibition of NO production, with an $EC_{50}$ of 2.07-5.41 µmol/L. Compared with the positive control group of quercetin (with an $EC_{50}$ of 9.56 µmol/L) and oxiconazole (with an $EC_{50}$ of 13.5 µmol/L), the inhibitory effect is stronger without significant cytotoxicity (cell viability >90%), which can be used to prepare drugs for the treatment of Alzheimer's disease.

11 Claims, 4 Drawing Sheets

3,4-METHYLENEDIOXYPHENYLIMIDAZO-LYLETHANONEXIME ETHER DERIVATIVE, PREPARATION METHOD AND USE THEREOF, AND DRUG FOR THE TREATMENT OF ALZHEIMER'S DISEASE

CROSS REFERENCE TO RELATED APPLICATION

This patent application claims the benefit and priority of Chinese Patent Application No. 202111412170.7, filed on Nov. 25, 2021, the disclosure of which is incorporated by reference herein in its entirety as part of the present application.

TECHNICAL FIELD

The present disclosure relates to the technical field of preparation of acetophenone oxime ether compounds, in particular to 3,4-methylenedioxyphenylimidazolylethanonexime ether derivatives, a preparation method and use thereof, and a drug for the treatment of Alzheimer's disease.

BACKGROUND ART

Alzheimer's disease (AD) is one of the most common diseases that cause dementia in the elderly, accounting for 75% of all dementia patients. Alzheimer's disease is a heterogeneous and pathophysiologically complicated neurodegenerative disease. In most cases, it is multi-genotype (sporadic AD), and a few are mono-genotype (0.5% autosomal dominant inheritance AD). The clinical manifestations of AD are often accompanied by cognitive impairment, dysfunction, loss of independent living ability, etc. The incidence of cognitive impairment increases with age. At present, the incidence of AD patients in China has risen sharply with the aging of the Chinese population, which is one of the great challenges facing the geriatrics community. The discovery of effective preventive or therapeutic drugs has become one of the major tasks of today's medical workers.

Neuroinflammation, a hallmark factor of Alzheimer's disease, is caused by activated microglia. Microglia are primary immune cells that play a vital role in the innate immune response of the normal brain and central nervous system (CNS). In a healthy brain, these cells are in a static or inactive state. However, microglia are particularly sensitive to change in their microenvironment and are easily activated during infection or injury. When these cells recognize a threat or injury to the CNS, they become active, changing size and shape and then migrating to the site of injury. Chronic and sustained activation of microglia can result in the increased inflammatory mediators, including nitric oxide (NO), tumor necrosis factor alpha (TNF-α) and interleukin 1β(IL-1β), creating a neurotoxic environment that ultimately promotes AD progression. Currently, only several FDA-approved anti-AD drugs (such as cholinesterase inhibitors: donepezil, rivastigmine, galantamine, and tacrine, and N-methyl-d-aspartic acid: memantine) are clinically available. Nevertheless, these drugs offer only partial alleviation of symptoms, and cannot stop or reverse the progression of the disease.

SUMMARY

In view of this, the present disclosure provides (Z)-3,4-methylenedioxyphenylimidazolylethanonexime ether derivatives, a preparation method and use thereof, and a drug for the treatment of Alzheimer's disease. The (Z)-3,4-methylenedioxyphenylimidazolylethanonexime ether derivatives provided by the present disclosure showed a significant effect on the inhibition of NO production without significant cytotoxicity, and possessed significant improvement effect on the decline in learning and memory ability and working memory ability, and can effectively alleviate the anxiety symptoms caused by AD, which can be used to prepare drugs for the treatment of Alzheimer's disease.

In order to solve the above technical problems, the present disclosure provides (Z)-3,4-methylenedioxyphenylimidazolylethanonexime ether derivatives having a structure represented by formula I:

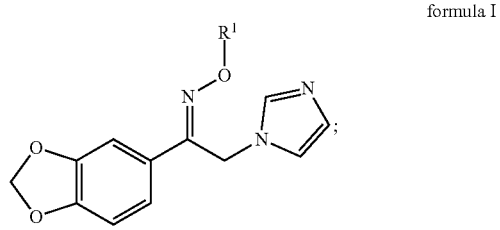

formula I

Wherein, $R_1$ is one of a $C_3$-$C_5$ alkene group, a $C_3$-$C_5$ alkynyl group, a benzyl group and a substituted benzyl group, and the substituted benzyl group is a haloalkyl substituted benzyl group and/or a cyano substituted benzyl group.

In some embodiments, the (Z)-3,4-methylenedioxyphenylimidazolylethanonexime ether derivatives have any one of the structures represented by formula I-1-I-9:

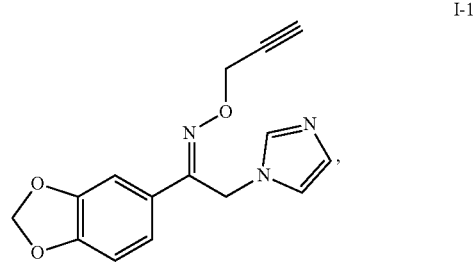

I-1

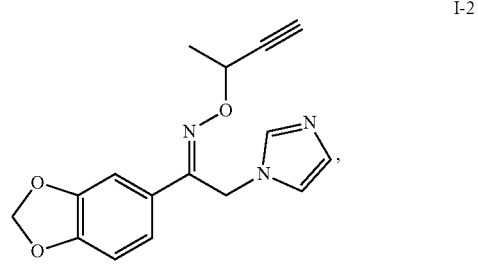

I-2

I-3 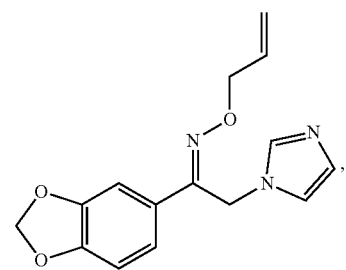

I-4 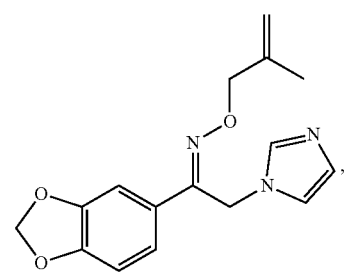

I-5 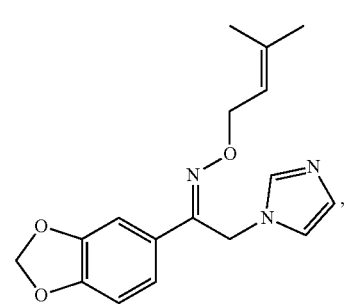

I-6 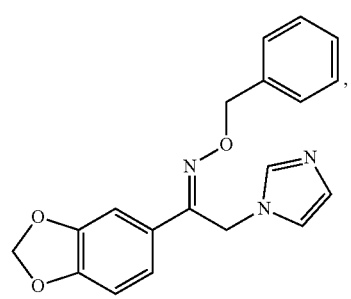

I-7 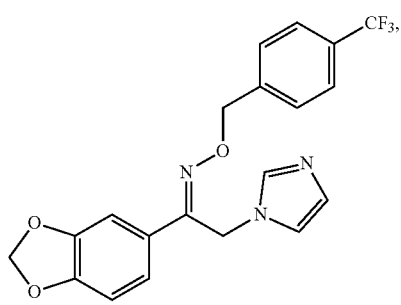

I-8 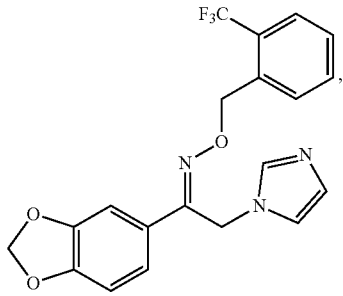

I-9 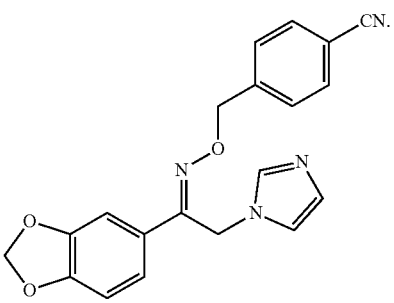

The present disclosure provides a method for preparing the (Z)-3,4-methylenedioxyphenylimidazolylethanonexime ether derivatives described in above technical schemes, comprising the steps of:

Mixing and subjecting 1-(benzo[d][1,3]dioxol-5-yl)-2-(1H-imidazol-1-yl)ethan-1-one oxime, an alkali metal hydride, a halogenated compound and an organic solvent to a nucleophilic substitution reaction to obtain the (Z)-3,4-methylenedioxyphenylimidazolylethanonexime ether derivatives;

The halogenated compounds are selected from the group consisting of a $C_3$-$C_5$ halogenated olefin, a $C_3$-$C_5$ halogenated alkyne, a benzyl halide, and a substituted benzyl halide; and the substituted benzyl halide is a halogenated alkyl substituted benzyl halide and/or a cyano substituted benzyl halide.

In some embodiments, a method for preparing 1-(benzo [d][1,3]dioxol-5-yl)-2-(1H-imidazol-1-yl)ethan-1-one oxime includes steps of:

Mixing and subjecting 1-(benzo[d][1,3]dioxol-5-yl)-2-(1H-imidazol-1-yl)ethan-1-one, an alkali metal salt of an organic acid, hydroxylamine hydrochloride, a water scavenger and an organic solvent to an imidization reaction to obtain the 1-(benzo[d][1,3]dioxol-5-yl)-2-(1H-imidazol-1-yl)ethan-1-one oxime.

In some embodiments, a method for preparing 1-(benzo [d][1,3]dioxol yl)-2-(1H-imidazol-1-yl)ethan-1-one includes steps of:

Mixing and subjecting 2-halo-1-(benzo[d][1,3]dioxol-5-yl)ethan-1-one, 1H-imidazole, an inorganic weak base and an organic solvent to a N-alkylation reaction to obtain 1-(benzo[d][1,3]dioxol-5-yl)-2-(1H-imidazol-1-yl)ethan-1-one.

In some embodiments, a mass ratio of 1-(benzo[d][1,3] dioxol-5-yl)-2-(1H-imidazol-1-yl)ethan-1-one oxime, the halogenated compound and the alkali metal hydride is 2: (0.75-1.2): 0.2.

In some embodiments, a mass ratio of 1-(benzo[d][1,3] dioxol-5-yl)-2-(1H-imidazol-1-yl)ethan-1-one, the alkali metal salt of an organic acid and the water scavenger is 2:

(1.5-1.6): 1, and a mass ratio of 1-(benzo[d][1,3]dioxin-5-yl)-2-(1H-imidazol-1-yl)ethan-1-one and hydroxylamine hydrochloride is 2: (1.3-1.4);

A holding temperature of the imidization reaction is 70-95° C.; a holding time of the imidization reaction is 12-15 h; and the imidization reaction is carried out under reflux.

The present disclosure provides a use of the (Z)-3,4-methylenedioxyphenylimidazolylethanonexime ether derivatives described in above technical schemes or the (Z)-3,4-methylenedioxyphenylimidazolylethanonexime ether derivatives prepared by the method described in above technical schemes in the preparation of drugs for the treatment of Alzheimer's disease.

The present disclosure provides a drug for the treatment of Alzheimer's disease comprising a (Z)-3,4-methylenedioxyphenylimidazolylethanonexime ether derivative and a pharmaceutically acceptable excipient, the (Z)-3,4-methylenedioxyphenylimidazolylethanonexime ether derivatives is the (Z)-3,4-methylenedioxyphenylimidazolylethanonexime ether derivatives described in above technical schemes or the (Z)-3,4-methylenedioxyphenylimidazolylethanonexime ether derivatives prepared by the method described in above technical schemes.

In some embodiments, a dosage form of the drug comprises an injection.

The present disclosure provides a (Z)-3,4-methylenedioxyphenylimidazolylethanonexime ether derivatives having a structure represented by formula I:

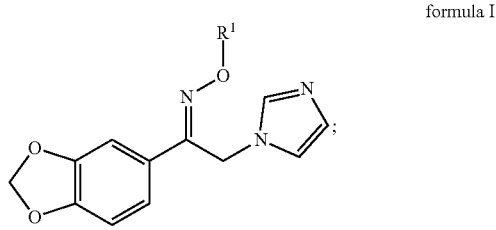

formula I

Wherein, $R_1$ is one of a $C_3$-$C_5$ alkene group, a $C_3$-$C_5$ alkynyl group, a benzyl group and a substituted benzyl group; and the substituted benzyl group is a haloalkyl substituted benzyl group and/or a cyano substituted benzyl group.

A dioxolane group on a benzene ring in the chemical structure of the (Z)-3,4-methylenedioxyphenylimidazolylethanonexime ether derivatives provided by the present disclosure can effectively improve the inhibitory activity of NO, and an acetophenone oxime structure with an imidazole ring has excellent anti-inflammatory effects. The results of the examples showed that the (Z)-3,4-methylenedioxyphenylimidazolylethanonexime ether derivatives provided by the present disclosure showed a significant effect on the inhibition of NO production, with an $EC_{50}$ of 2.07-5.41 μmol/L. Compared with the positive control group of quercetin (with an $EC_{50}$ of 9.56 μmol/L) and oxiconazole (with an $EC_{50}$ of 13.5 μmol/L), the inhibitory effect was stronger without significant cytotoxicity (cell viability >90%). Moreover, using the (Z)-3,4-methylenedioxyphenylimidazolylethanonexime ether derivatives provided by the present disclosure as an injection to perform a learning and memory ability test, a working memory ability test and an anxiety symptoms treatment test on AD model mice, it was found that the derivative I-1 provided by the present disclosure possessed significant improvement effect on the decline in learning and memory ability and working memory ability, and can effectively alleviate the anxiety symptoms, which can be used to prepare drugs for the treatment of Alzheimer's disease.

The present disclosure provides scientific experimental data for the development of new drugs for the treatment of Alzheimer's disease, as well as the clinical personalized drugs for the treatment of Alzheimer's disease.

DETAILED DESCRIPTION OF THE EMBODIMENTS

Figure 1:
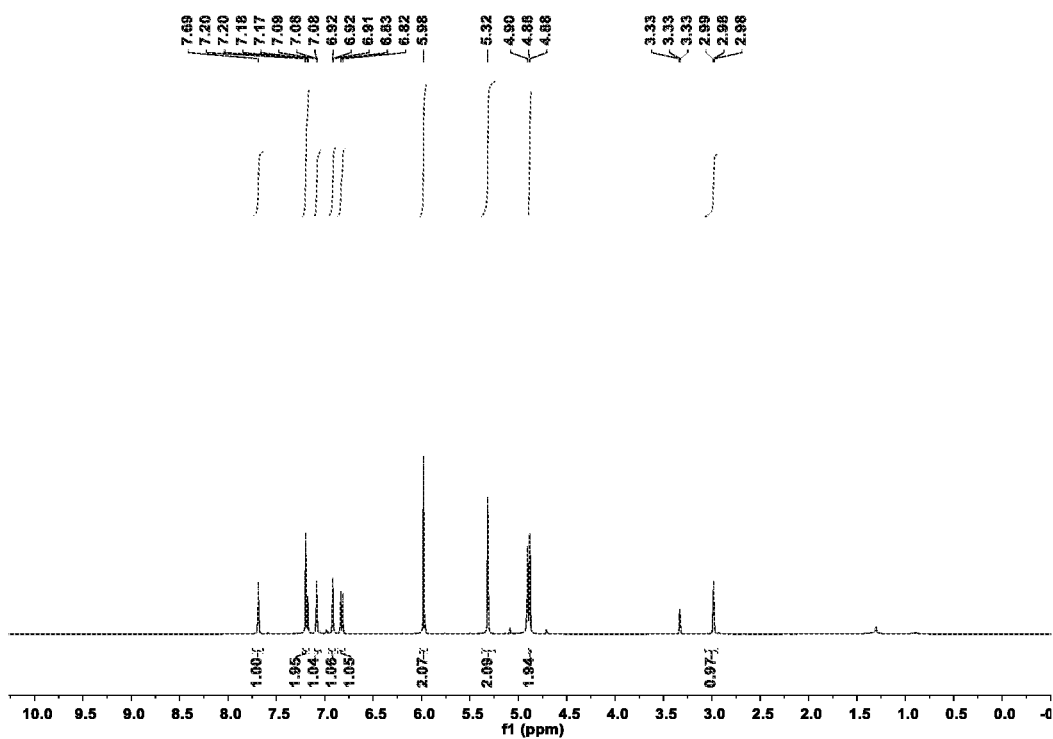
FIG. 1 is a $^1$H NMR (400 MHz, CDCl$_3$) spectrum of compound I-1 prepared in Example 1 of the present disclosure.

The present disclosure provides a (Z)-3,4-methylenedioxyphenylimidazolylethanonexime ether derivatives having a structure represented by formula I:

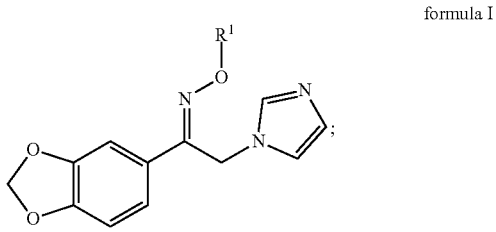

formula I

Wherein, $R_1$ is one of a $C_3$-$C_5$ alkene group, a $C_3$-$C_5$ alkynyl group, a benzyl group and a substituted benzyl group; and the substituted benzyl group is a haloalkyl substituted benzyl group and/or a cyano substituted benzyl group.

In the present disclosure, $R_1$ is preferably one of a $C_3$-$C_5$ linear alkene group, a $C_3$-$C_5$ branched alkene group, a $C_3$-$C_5$ linear alkynyl group, a $C_3$-$C_5$ branched alkynyl group, a benzyl group, and a substituted benzyl group; the substituted benzyl group is a haloalkyl substituted benzyl group and/or a cyano substituted benzyl group. In the present disclosure, a halogen substituent in the haloalkyl substituted benzyl group is preferably one of chlorine and fluorine; and an alkyl group in the haloalkyl substituted benzyl group is preferably one of methyl and ethyl.

In the present disclosure, the (Z)-3,4-methylenedioxyphenylimidazolylethanonexime ether derivatives have any one of the structures represented by formula I-1-I-9:

I-1
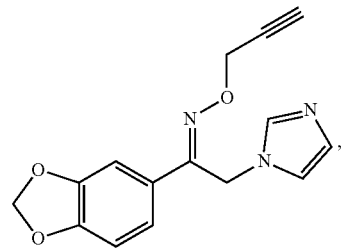

I-2
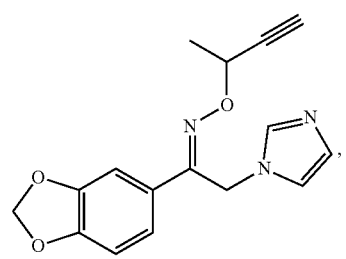

I-3
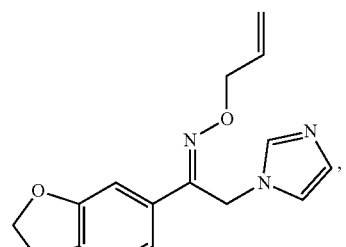

I-4
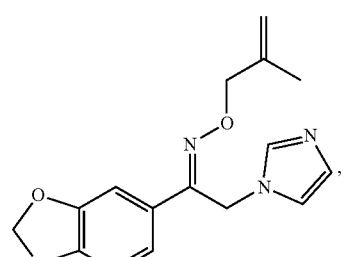

I-5
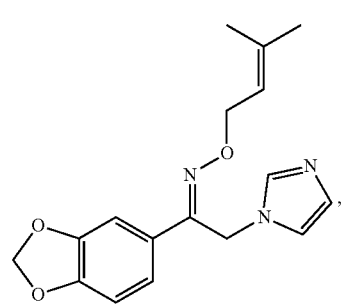

-continued

I-6
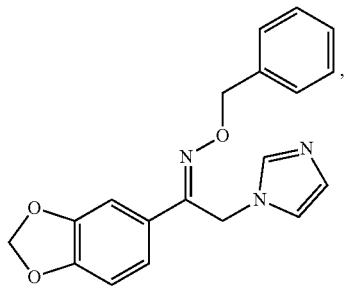

I-7
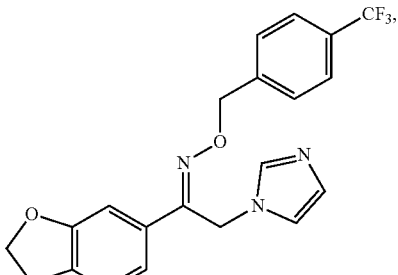

I-8
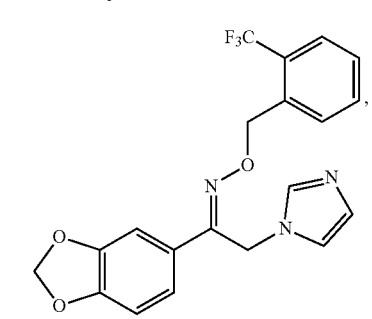

I-9
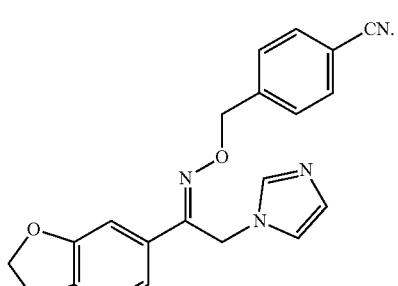

The present disclosure provides a method for preparing the (Z)-3,4-methylenedioxyphenylimidazolylethanonexime ether derivatives described in above technical schemes, comprising steps of:

Mixing and subjecting 1-(benzo[d][1,3]dioxol-5-yl)-2-(1H-imidazol-1-yl)ethan-1-one oxime, an alkali metal hydride, a halogenated compound and an organic solvent to a nucleophilic substitution reaction to obtain the (Z)-3,4-methylenedioxyphenylimidazolylethanonexime ether derivatives;

The halogenated compound is selected from the group consisting of a $C_3$-$C_5$ halogenated olefin, a $C_3$-$C_5$ halogenated alkyne, a benzyl halide, and a substituted benzyl halide; and the substituted benzyl halide is a halogenated alkyl substituted benzyl halide and/or a cyano substituted benzyl halide.

The present disclosure has no special requirements on the source of the 1-(benzo[d][1,3]dioxol-5-yl)-2-(1H-imidazol- 1-yl)ethan-1-one oxime, and any commercially available product or prepared product can be used.

In the present disclosure, a method for preparing 1-(benzo[d][1,3]dioxol-5-yl)-2-(1H-imidazol-1-yl)ethan-1-one oxime preferably includes steps of:

Mixing and subjecting 1-(benzo[d][1,3]dioxol-5-yl)-2-(1H-imidazol yl)ethan-1-one, an alkali metal salt of an organic acid, hydroxylamine hydrochloride, a water scavenger and an organic solvent to an imidization reaction to obtain the 1-(benzo[d][1,3]dioxol-5-yl)-2-(1H-imidazol-1-yl)ethan-1-one oxime.

The present disclosure has no special requirements on the source of the 1-(benzo[d][1,3]dioxol-5-yl)-2-(1H-imidazol-1-yl)ethan-1-one, and any commercially available product or prepared product can be used.

In the present disclosure, a method for preparing 1-(benzo[d][1,3]dioxol-5-yl)-2-(1H-imidazol-1-yl)ethan-1-one preferably includes steps of:

Mixing and subjecting 2-halo-1-(benzo[d][1,3]dioxol-5-yl)ethan-1-one, 1H-imidazole, an inorganic weak base and an organic solvent to a N-alkylation reaction to obtain 1-(benzo[d][1,3]dioxol-5-yl)-2-(1H-imidazol-1-yl)ethan-1-one.

The present disclosure has no special requirements on the source of the 2-halo-1-(benzo[d][1,3]dioxol-5-yl)ethan-1-one, and any commercially available product can be used.

In the present disclosure, 2-halo-1-(benzo[d][1,3]dioxol-5-yl)ethan-1-one preferably includes one of 2-bromo-1-(benzo[d][1,3]dioxol-5-yl)ethan-1-one and 2-chloro-1-(benzo[d][1,3]dioxol-5-yl)ethane-1-one.

In the present disclosure, the inorganic weak base preferably includes alkali metal carbonate. In a specific embodiment of the present disclosure, the inorganic weak base is preferably sodium carbonate.

In the present disclosure, the inorganic weak base preferably provides an alkaline reaction environment for the N-alkylation reaction.

In a specific embodiment of the present disclosure, a first organic solvent is preferably N,N-dimethylformamide (DMF). The present disclosure does not have any special requirements on the amount of the first organic solvent, as long as the 2-halo (benzo[d][1,3]dioxol-5-yl)ethane-1-one, 1H-imidazole, and the inorganic weak base can be fully dissolved. In a specific embodiment of the present disclosure, a ratio of an amount-of-substance of 1H-imidazole to a volume of the first organic solvent is preferably 0.702 mmol: 1 mL.

In the present disclosure, a mass ratio of 1H-imidazole, 2-halo-1-(benzo[d][1,3]dioxol-5-yl)ethan-1-one and the inorganic weak base is preferably 1: (1.9-2): (1.5-1.7), and more preferably 1: (1.92-1.98): (1.55-1.67).

In the present disclosure, a first mixing is preferably dissolving 1H-imidazole and the inorganic weak base in the first organic solvent to obtain an alkaline imidazole solution, and mixing the alkaline imidazole solution and 2-halo-1-(benzo[d][1,3]dioxol-5-yl)ethan-1-one.

In the present disclosure, 1H-imidazole and the inorganic weak base are dissolved in the first organic solvent to obtain an alkaline imidazole solution. In the present disclosure, a holding temperature for dissolution is preferably room temperature, a holding time for dissolution is preferably 0.5 h, and the dissolution is preferably carried out under stirring.

After obtaining the alkaline imidazole solution, the alkaline imidazole solution is mixed with 2-halo-1-(benzo[d][1,3]dioxol-5-yl)ethan-1-one. In the present disclosure, a holding temperature for mixing the alkaline imidazole solution and 2-halo-1-(benzo[d][1,3]dioxol-5-yl)ethan-1-one is preferably 45-52° C., and more preferably 50° C.

In the present disclosure, a holding temperature of the N-alkylation reaction is preferably 40-60° C., and more preferably 50° C.

In the present disclosure, a holding time of the N-alkylation reaction is preferably 2-5 h, and more preferably 3 h.

In the present disclosure, the N-alkylation reaction is preferably carried out under stirring. The present disclosure has no special requirements on the specific implementation process of the stirring.

In the present disclosure, an equation of the N-alkylation reaction is shown in formula II:

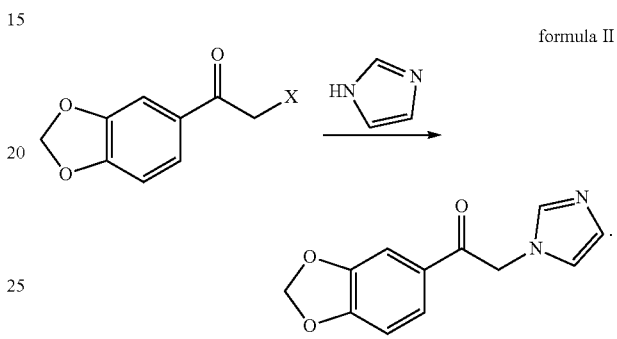

formula II

In the formula II, X is a halogen, preferably Br or Cl.

In the present disclosure, after the N-alkylation reaction, an N-alkylation reaction solution is obtained. In the present disclosure, the N-alkylation reaction solution is preferably subjected to post-treatment to obtain the 1-(benzo[d][1,3]dioxol-5-yl)-2-(1H-imidazol-1-yl)ethan-1-one.

In the present disclosure, the post-treatment preferably includes washing with water, extracting, extractant removing and purifying in sequence. In the present disclosure, the specific implementation of washing with water is preferably conducted by mixing the N-alkylation reaction solution and water for washing. The present disclosure does not have any special requirements on a volume ratio of water and the N-alkylation reaction solution. In the present disclosure, times of washing with water is preferably one. In the present disclosure, the N-alkylation reaction solution after washing with water is preferably subjected to extraction. In the present disclosure, the extractant is preferably an organic solvent, and more preferably dichloroethane. The present disclosure has no special requirements on a volume ratio of the extractant and the N-alkylation reaction solution after washing with water. In the present disclosure, an extraction phase after extraction is preferably subjected to extractant removing. In the present disclosure, the specific implementation of the extractant removing is preferably vacuum evaporation, and the present disclosure has no special requirements on the specific implementation of the vacuum evaporation. In the present disclosure, a solid product after extractant removing is preferably subjected to purifying. In the present disclosure, the purifying is preferably conducted by column chromatography. The present disclosure does not have special requirements on the specific implementation of the purifying by column chromatography.

In the present disclosure, the alkali metal salt of an organic acid is preferably an alkali metal of acetate, and more preferably sodium acetate.

In the present disclosure, the alkali metal salt of an organic acid provides an alkaline environment for the imidization reaction.

In the present disclosure, the water scavenger is preferably anhydrous magnesium sulfate.

In the present disclosure, a second organic solvent is preferably a lower alcohol; in a specific embodiment of the present disclosure, the second organic solvent is preferably ethanol. The present disclosure does not have any special requirements on an amount of the second organic solvent, as long as 1-(benzo[d][1,3]dioxol-5-yl)-2-(1H-imidazol-1-yl)ethan-1-one, the alkali metal salt of an organic acid, hydroxylamine hydrochloride and the water scavenger can be fully dissolved.

In the present disclosure, a mass ratio of 1-(benzo[d][1,3]dioxol-5-yl)-2-(1H-imidazol-1-yl)ethan-1-one, the alkali metal salt of an organic acid and the water scavenger is preferably 2: (1.5-1.6): 1, and more preferably (1.2-1.7): (1.52-1.58): 1.

In the present disclosure, a mass ratio of 1-(benzo[d][1,3]dioxol-5-yl)-2-(1H-imidazol-1-yl)ethan-1-one and hydroxylamine hydrochloride is preferably 2: (1.3-1.4), and more preferably 1:(0.66-0.68).

In the present disclosure, a second mixing is preferably conducted by dissolving 1-(benzo[d][1,3]dioxol-5-yl)-2-(1H-imidazol-1-yl)ethan-1-one, the alkali metal salt of an organic acid, hydroxylamine hydrochloride and the water scavenger in the second organic solvent. The present disclosure does not have any special requirements on an order of dissolving 1-(benzo[d][1,3]dioxol-5-yl)-2-(1H-imidazol yl)ethan-1-one, the alkali metal salt of an organic acid, hydroxylamine hydrochloride and the water scavenger.

In the present disclosure, a holding temperature of the imidization reaction is preferably 70-95° C., and more preferably 75-90° C. In the present disclosure, a holding time of the imidization reaction is preferably 12-15 h, and more preferably 14 h. In the present disclosure, the imidization reaction is preferably carried out under heating and refluxing. The present disclosure has no special requirements on the specific implementation of the heating and refluxing.

In the present disclosure, an equation of the imidization reaction is shown in formula III:

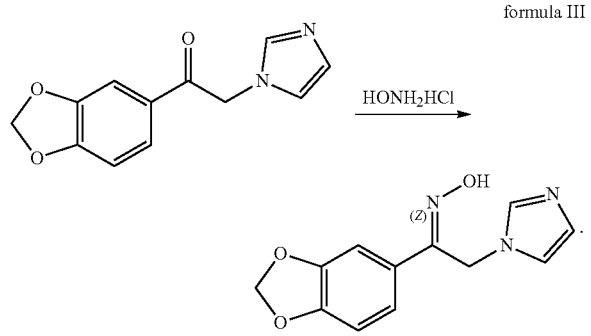

formula III

In the present disclosure, an imidization reaction solution is obtained after the imidization reaction. In the present disclosure, the imidization reaction solution is preferably subjected to post-treatment to obtain the 1-(benzo[d][1,3]dioxol-5-yl)-2-(1H-imidazol-1-yl)ethan-1-one oxime.

In the present disclosure, the post-treatment preferably includes solvent removing, dissolving, extracting, extractant removing and purifying in sequence. In the present disclosure, the specific implementation of solvent removing is preferably vacuum evaporation, and the present disclosure has no special requirements on the specific implementation of the vacuum evaporation. In the present disclosure, a solid product obtained after solvent removing is preferably subjected to dissolving with water to obtain an aqueous solution. The present disclosure has no special requirements on an amount of water as long as the solid product can be fully dissolved. In the present disclosure, the obtained aqueous solution is preferably subjected to extracting. In the present disclosure, the extractant is preferably an organic solvent, and more preferably dichloroethane. The present disclosure has no special requirements on the volume ratio of the extractant and the aqueous solution. In the present disclosure, an extraction phase after extraction is preferably subjected to extractant removing. In the present disclosure, the specific implementation of the extractant removing is preferably vacuum evaporation. The present disclosure does not have special requirements on the specific implementation of the vacuum evaporation. In the present disclosure, a solid product after removing the extractant is preferably subjected to purifying. In the present disclosure, the purifying is preferably conducted by column chromatography. The present disclosure does not have special requirements on the specific implementation of the purifying by column chromatography.

In a specific embodiment of the present disclosure, the alkali metal hydride is preferably sodium hydride.

In the present disclosure, the halogenated compound is selected from the group consisting of $C_3$-$C_5$ halogenated alkenes, $C_3$-$C_5$ halogenated alkynes, benzyl halides, and substituted benzyl halides; and the substituted benzyl halides are halogenated alkyl substituted benzyl halides, and/or cyano substituted benzyl halides.

In a specific embodiment of the present disclosure, the halogenated compound is preferably a brominated compound, and in an embodiment of the present disclosure, it is preferably one of

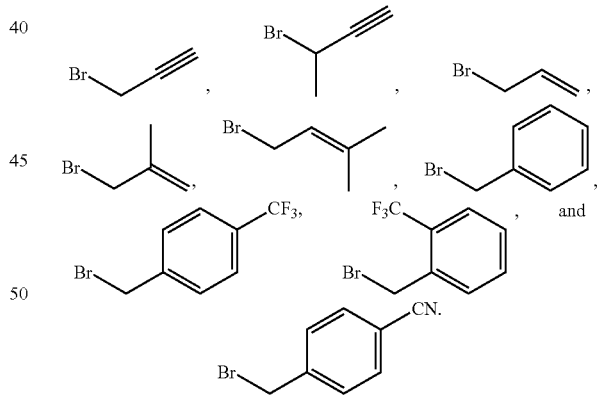

In a specific embodiment of the present disclosure, a third organic solvent is preferably tetrahydrofuran (THF). The present disclosure does not have special requirements on an amount of the third organic solvent, as long as 1-(benzo[d][1,3]dioxol-5-yl)-2-(1H-imidazol-1-yl)ethan-1-one oxime, the alkali metal hydride and the halogenated compound can be fully dissolved.

In the present disclosure, a mass ratio of 1-(benzo[d][1,3]dioxol-5-yl) (1H-imidazol-1-yl)ethan-1-one oxime, the halogenated compound and the alkali metal hydride is preferably 2: (0.75-1.2): 0.2, and more preferably 1:(0.4-0.55): 0.1.

In the present disclosure, a third mixing is preferably conducted by dissolving 1-(benzo[d][1,3]dioxol-5-yl)-2-(1H-imidazol-1-yl)ethan-1-one oxime in the third organic solvent to obtain a 1-(benzo[d][1,3]dioxol-5-yl)-2-(1H-imidazol-1-yl)ethan-1-one oxime solution; mixing the 1-(benzo[d][1,3]dioxol-5-yl)-2-(1H-imidazol-1-yl)ethan-1-one oxime solution with the alkali metal hydride to obtain an intermediate; and mixing the intermediate with the halogenated compound.

In the present disclosure, the 1-(benzo[d][1,3]dioxol-5-yl)-2-(1H-imidazol-1-yl)ethan-1-one oxime is dissolved in the third organic solvent to obtain a 1-(benzo[d][1,3]dioxol-5-yl)-2-(1H-imidazol-1-yl)ethan-1-one oxime solution. In the present disclosure, the dissolving is preferably carried out at room temperature.

After obtaining the 1-(benzo[d][1,3]dioxin-5-yl)-2-(1H-imidazol-1-yl)ethan-1-one oxime solution, it is mixed with the alkali metal hydride to obtain an intermediate. In the present disclosure, a holding temperature of mixing the 1-(benzo[d][1,3]dioxol-5-yl)-2-(1H-imidazol-1-yl)ethan-1-one oxime solution with the alkali metal hydride is preferably 0° C., a holding time of the mixing is 0.5 h, and the mixing is preferably carried out under stirring.

After obtaining the intermediate, it is mixed with the halogenated compound. In the present disclosure, a holding temperature for mixing the intermediate mixture with the halogenated compound is preferably 0° C., a holding time for mixing the intermediate mixture with the halogenated compound is 20 min, and the mixing is preferably carried out under stirring.

In the present disclosure, a holding temperature of the nucleophilic substitution reaction is preferably room temperature, a holding time of the nucleophilic substitution reaction is preferably 5-8 h, and more preferably 6 h. The nucleophilic substitution reaction is preferably carried out under stirring.

In the present disclosure, the nucleophilic substitution reaction is shown in formula IV:

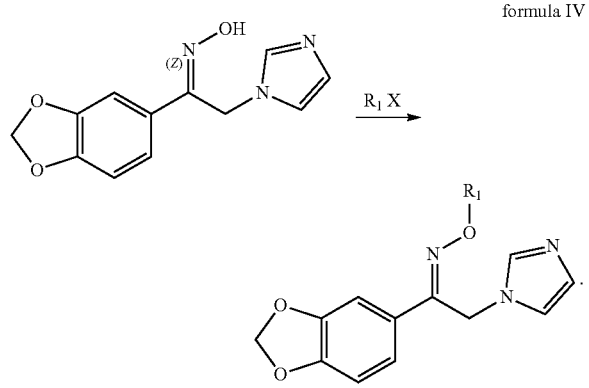

formula IV

In the present disclosure, a nucleophilic substitution reaction solution is obtained after the nucleophilic substitution reaction. In the present disclosure, the nucleophilic substitution reaction solution is preferably subjected to post-treatment to obtain the (Z)-3,4-methylenedioxyphenylimidazolylethanonexime ether derivatives.

In the present disclosure, the post-treatment preferably includes solvent removing, dissolving, extracting, extractant removing, and purifying in sequence. In the present disclosure, the specific implementation of the solvent removing is preferably vacuum evaporation, and the present disclosure has no special requirements on the specific implementation of the vacuum evaporation. In the present disclosure, a solid product obtained after solvent removing is preferably subjected to dissolving with water to obtain an aqueous solution. The present disclosure has no special requirements on an amount of water as long as the solid product can be fully dissolved. In the present disclosure, the obtained aqueous solution is preferably subjected to extracting. In the present disclosure, the extractant is preferably an organic solvent, and more preferably dichloroethane. The present disclosure has no special requirements on a volume ratio of the extractant and the aqueous solution. In the present disclosure, an extraction phase is preferably subjected to extractant removing. In the present disclosure, the specific implementation of extractant removing is preferably vacuum evaporation. The present disclosure has no special requirements on the specific implementation of the vacuum evaporation. In the present disclosure, a solid product after extractant removing is preferably subjected to purifying. In the present disclosure, the purifying is preferably conducted by column chromatography. The present disclosure does not have special requirements on the specific implementation of the purifying by column chromatography.

The present disclosure provides a use of the (Z)-3,4-methylenedioxyphenylimidazolylethanonexime ether derivatives described in the above technical schemes or the (Z)-3,4-methylenedioxyphenylimidazolylethanonexime ether derivatives prepared by the method described in the above technical schemes in preparing drugs for the treatment of Alzheimer's disease.

The present disclosure provides a drug for the treatment of Alzheimer's disease comprising a (Z)-3,4-methylenedioxyphenylimidazolylethanonexime ether derivative I-1 and a pharmaceutically acceptable excipient, I-1 is the (Z)-3,4-methylenedioxyphenylimidazolylethanonexime ether derivative described in above technical schemes or the (Z)-3,4-methylenedioxyphenylimidazolylethanonexime ether derivative prepared by the method described in above technical schemes.

In the present disclosure, the pharmaceutically acceptable excipients are preferably pharmaceutical excipients that do not affect or contribute to the efficacy of the drug.

In the present disclosure, a dosage form of the drug preferably includes an injection.

In the present disclosure, when the dosage form of the drug for the treatment of Alzheimer's disease is specifically an injection, the pharmaceutically acceptable excipient is preferably a mixture of Tween 80, ethanol and water, a mass percentage of Tween 80 in the mixture is preferably 5%, a mass percentage of ethanol is preferably 5%, and a mass percentage of water is preferably 90%.

In the injection, a mass percentage of compound I-1 is preferably 0.3%.

In order to further illustrate the present disclosure, the technical schemes provided by the present disclosure will be described in detail below in conjunction with embodiments, but they should not be understood as limiting the protection scope of the present disclosure.

Example 1

Imidazole (3.510 mmol), and potassium carbonate ($K_2CO_3$, 2.684 mmol) in 5 mL DMF was stirred at room temperature for 0.5 h, then 2-bromo (benzo[d][1,3]dioxol-5-yl)ethan-1-one (2.066 mmol) was added thereto. The mixture was stirred at 50° C. for 3 h. After completion, the solvent was evaporated under reduced pressure. The residue was diluted with water, and extracted with dichloromethane (DCM), organic layer was then collected, dried over anhydrous MgSO$_4$, filtered, concentrated and purified by column chromatography to obtain 1-(benzo[d][1,3]dioxol-5-yl)-2-(1H-imidazol-1-yl)ethan-1-one with a yield of 85%, and the N-alkylation reaction is shown in formula V:

formula V

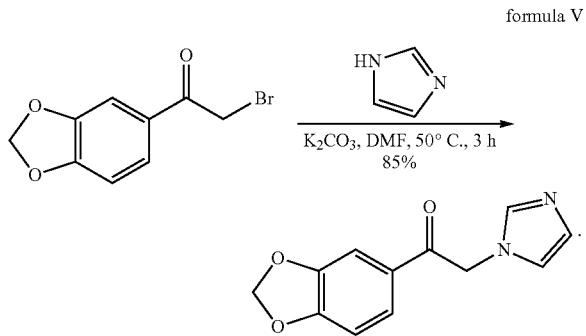

A mixture of 1-(benzo[d][1,3]dioxol-5-yl)-2-(1H-imidazol-1-yl)ethan-1-one (0.695 mmol), sodium acetate (0.719 mmol), hydroxylamine hydrochloride (NH$_2$OH·HCl, 0.719 mmol), and anhydrous magnesium sulfate (50 mg) in 4 mL of anhydrous alcohol was stirred for 14 h at 75° C. After completion, the solvent was evaporated under reduced pressure, the residue was then diluted with water and extracted with dichloromethane (DCM). The combined organic extracts were washed with brine, dried over anhydrous Na$_2$SO$_4$, filtered, and concentrated under reduced pressure. The crude product was purified by column chromatography to obtain 1-(benzo[d][1,3]dioxol-5-yl)-2-(1H-imidazol-1-yl)ethan-1-one oxime, and the imidization reaction is shown in formula VI:

formula VI

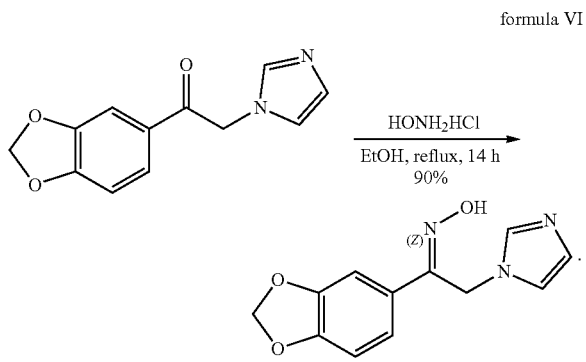

To a stirred mixture of 1-(benzo[d][1,3]dioxol-5-yl)-2-(1H-imidazol yl)ethan-1-one oxime (0.366 mmol) and NaH (0.476 mmol) in THF (2 mL) was slowly added propargyl bromide

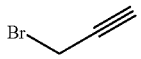

(0.622 mmol) at 0° C. and stirred for 20 min. Then the mixture was warmed at room temperature and stirred for another 6 h, the reaction was monitored by TLC. Next, the solvent was evaporated under reduced pressure, then water was poured into the mixture and extracted with EtOAc. The organic layer was collected, dried over MgSO$_4$, filtered and concentrated under reduced pressure to give the crude product. The residue was purified by column chromatography to obtain a (Z)-3,4-methylenedioxyphenylimidazolylethanonexime ether derivative, denoted as I-1; a white solid with a yield of 74%; m.p. 189.6-190.4° C. $^1$H NMR (400 MHz, MeOD) δ 7.69 (s, 1H), 7.20 (s, 1H), 7.19 (dd, J=7.7, 1.8 Hz, 1H), 7.08 (m, 1H), 6.92 (m, 1H), 6.83 (d, J=7.7 Hz, 1H), 5.98 (s, 2H), 5.32 (s, 2H), 4.88 (d, J=2.4 Hz, 2H), 2.98 (t, J=2.4 Hz, 1H); $^{13}$C NMR (100 MHz, MeOD) δ 153.34, 149.49, 148.26, 137.49, 127.66, 126.81, 120.97, 119.59, 107.74, 106.06, 101.61, 78.93, 75.15, 61.81, 39.97; HRMS (m/z): calculated for C$_{15}$H$_{13}$N$_3$O$_3$ [M+H]$^+$ 284.1039, found 284.1042.

Figure 2:
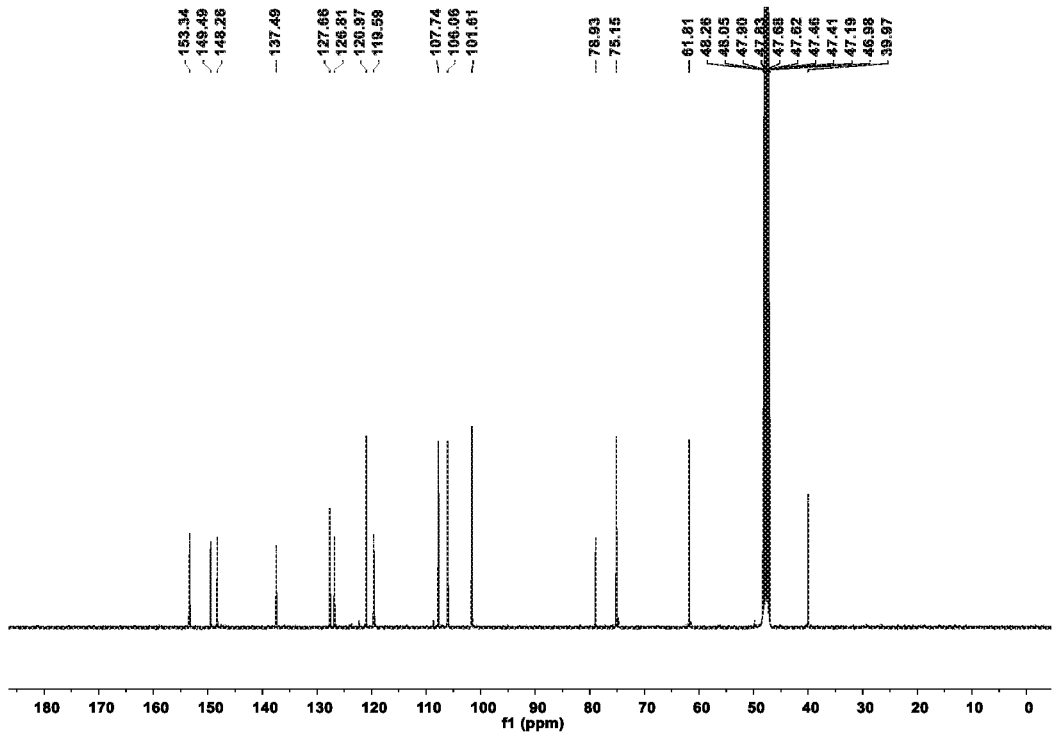
FIG. 2 is a $^{13}$C NMR (100 MHz, CDCl$_3$) spectrum of compound I-1 prepared in Example 1 of the present disclosure.
Figure 3:
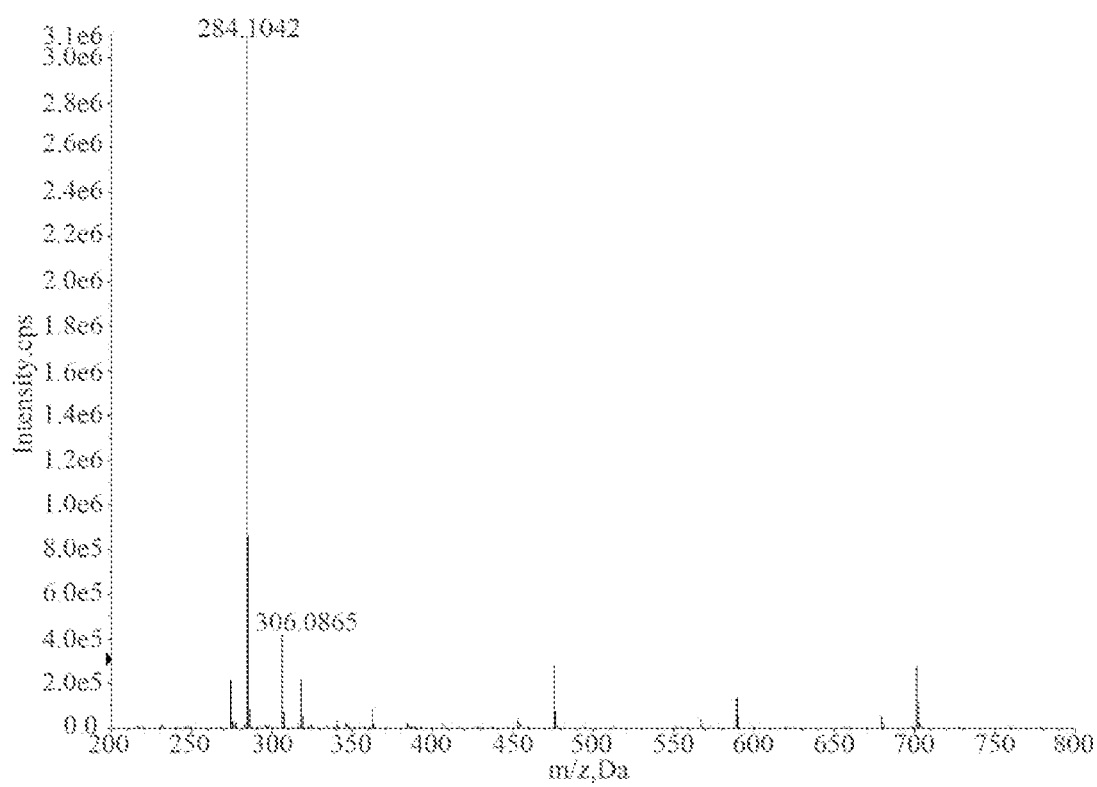
FIG. 3 is a high-resolution mass spectrum of compound I-1 prepared in Example 1 of the present disclosure.

FIG. 1 is a $^1$H NMR (400 MHz, CDCl$_3$) spectrum of compound I-1 prepared in Example 1 of the present disclosure; FIG. 2 is a $^{13}$C NMR (100 MHz, CDCl$_3$) spectrum of compound I-1 prepared in Example 1 of the present disclosure; FIG. 3 is a high-resolution mass spectrum of compound I-1 prepared in Example 1 of the present disclosure.

A reaction equation of the nucleophilic substitution reaction is shown in formula VII:

formula VII

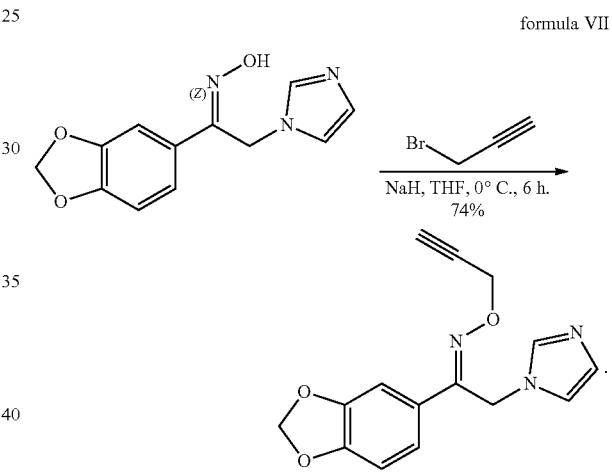

Example 2

The preparation steps are the same as in Example 1, except that the brominated compound

is replaced with to obtain a (Z)-3,4-methylenedioxyphenylimidazolylethanonexime ether derivative, denoted as 1-2, a white powder with a yield of 76%. $^1$H NMR (400 MHz, MeOD) δ 7.68 (s, 1H), 7.22-7.13 (m, 2H), 7.07 (s, 1H), 6.90 (s, 1H), 6.82 (s, 1H), 5.97 (s, 2H), 5.29 (s, 2H), 4.81 (q, J=2.4 Hz, 2H), 1.85 (t, J=2.3 Hz, 3H). $^{13}$C NMR (100 MHz, MeOD) δ 154.33, 150.80, 149.64, 138.92, 128.97, 128.38, 122.27, 121.00, 109.12, 107.40, 102.97, 84.03, 75.68, 63.81, 41.39, 3.16. HRMS (m/z): calculated for $C_{16}H_{15}N_3O_3$ [M+H]$^+$ 298.1186, found 298.1193.

Example 3

The preparation steps are the same as in Example 1, except that the brominated compound

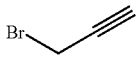

is replaced with

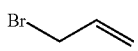

to obtain a (Z)-3,4-methylenedioxyphenylimidazolyletha-nonexime ether derivative, denoted as 1-3, a white powder with a yield of 57%. m.p. 154.3-154.9° C. $^1$H NMR (400 MHz, MeOD) δ 7.64 (s, 1H), 7.20-7.12 (m, 2H), 7.03 (s, 1H), 6.90 (s, 1H), 6.80 (d, J=8.1 Hz, 1H), 5.96 (s, 2H), 5.53-5.45 (m, 1H), 5.25 (s, 2H), 4.74 (d, J=7.2 Hz, 2H), 1.79 (s, 3H), 1.76 (s, 3H); $^{13}$C NMR (100 MHz, MeOD) δ 151.70, 149.19, 148.25, 148.24, 138.51, 127.48, 120.58, 120.57, 119.57, 107.69, 107.68, 105.82, 101.52, 70.85, 39.96, 24.56, 16.86; HRMS (m/z): calculated for $C_{17}H_{19}N_3O_3$ [M+H]$^+$ 314.1499, found 314.1508.

Example 4

The preparation steps are the same as in Example 1, except that the brominated compound

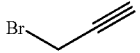

is replaced with

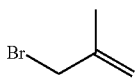

to obtain a compound 1-4, a white powder with a yield of 72%. m.p. 218.3-219.2° C. $^1$H NMR (400 MHz, MeOD) δ 7.66 (s, 1H), 7.16 (m, 2H), 7.04 (s, 1H), 6.91 (s, 1H), 6.81 (d, J=7.9 Hz, 1H), 5.96 (s, 2H), 5.31 (s, 2H), 5.01-4.91 (m, 2H), 4.67 (s, 2H), 1.77 (s, 3H). $^{13}$C NMR (100 MHz, MeOD) δ 151.97, 149.29, 148.27, 148.26, 141.69, 127.55, 127.33, 120.73, 120.72, 112.33, 107.72, 105.91, 101.56, 78.27, 40.13, 18.42. HRMS (m/z): calculated for $C_{16}H_{17}N_3O_3$ [M+H]$^+$ 300.1348, found 300.1352.

Example 5

The preparation steps are the same as in Example 1, except that the brominated compound

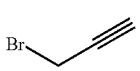

is replaced with

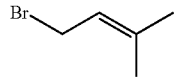

to obtain a compound 1-5, a white powder with a yield of 57%. m.p. 154.3-154.9° C. $^1$H NMR (400 MHz, MeOD) δ 7.64 (s, 1H), 7.20-7.12 (m, 2H), 7.03 (s, 1H), 6.90 (s, 1H), 6.80 (d, J=8.1 Hz, 1H), 5.96 (s, 2H), 5.53-5.45 (m, 1H), 5.25 (s, 2H), 4.74 (d, J=7.2 Hz, 2H), 1.79 (s, 3H), 1.76 (s, 3H). $^{13}$C NMR (100 MHz, MeOD) δ 151.70, 149.19, 148.25, 148.24, 138.51, 127.48, 120.58, 120.57, 119.57, 107.69, 107.68, 105.82, 101.52, 70.85, 39.96, 24.56, 16.86. HRMS (m/z): calculated for $C_{17}H_{19}N_3O_3$ [M+H]$^+$ 314.1499, found 314.1508.

Example 6

The preparation steps are the same as in Example 1, except that the brominated compound

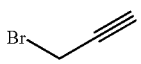

is replaced with

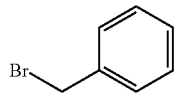

to obtain a compound 1-6, a white powder with a yield of 77%. m.p. 186.4-187.9° C. $^1$H NMR (400 MHz, MeOD) δ 7.59 (s, 1H), 7.43-7.26 (m, 5H), 7.19-7.09 (m, 2H), 6.96 (s, 1H), 6.87 (s, 1H), 6.80 (d, J=8.0 Hz, 1H), 5.95 (s, 2H), 5.27 (d, J=8.7 Hz, 4H). $^{13}$C NMR (100 MHz, MeOD) δ 152.33, 149.31, 148.25, 137.31, 128.22, 128.13, 128.12, 127.82, 127.41, 127.24, 120.75, 119.57, 107.72, 105.91, 101.55, 76.61, 40.14. HRMS (m/z): calculated for $C_{19}H_{17}N_3O_3$ [M+H]$^+$ 336.1342, found 336.1349.

Example 7

The preparation steps are the same as in Example 1, except that the brominated compound

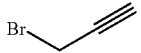

is replaced with

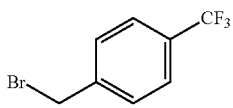 [SMILES: FC(F)(F)c1ccc(CBr)cc1]

to obtain a compound 1-7, a white powder with a yield of 75%. m.p. 121.8-122.7° C. $^1$H NMR (400 MHz, MeOD) δ 7.66 (d, J=8.3 Hz, 2H), 7.64 (s, 1H), 7.54 (d, J=8.0 Hz, 2H), 7.15 (m, 2H), 7.00 (s, 1H), 6.90 (s, 1H), 6.80 (d, J=8.5 Hz, 1H), 5.95 (s, 2H), 5.34 (d, J=6.1 Hz, 4H). $^{13}$C NMR (100 MHz, MeOD) δ 154.34, 150.83, 149.67, 143.43, 131.11 (q, $J_{C-F}$=32.3 Hz), 129.68, 128.98, 128.95, 128.46, 126.37 (q, $J_{C-F}$=3.9 Hz), 125.65 (d, $J_{C-F}$=271.2 Hz), 122.28, 120.96, 109.15, 107.33, 102.98, 76.87, 41.64. HRMS (m/z): calculated for $C_{20}H_{16}F_3N_3O_3$ [M+H]$^+$ 404.1216, found 404.1220.

Example 8

The preparation steps are the same as in Example 1, except that the brominated compound

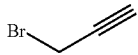

is replaced with

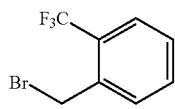

to obtain a compound 1-8, a white powder with a yield of 68%. m.p. 156.3-157.5° C. $^1$H NMR (400 MHz, MeOD) δ 7.73 (d, J=7.8 Hz, 1H), 7.64-7.54 (m, 3H), 7.50 (t, J=7.6 Hz, 1H), 7.18-7.12 (m, 2H), 6.99 (s, 1H), 6.89 (s, 1H), 6.80 (d, J=8.9 Hz, 1H), 5.95 (s, 2H), 5.46 (s, 2H), 5.32 (s, 2H). $^{13}$C NMR (100 MHz, MeOD) δ 154.31, 150.84, 149.68, 136.98, 133.41, 133.40, 131.92, 129.54, 129.26 (q, $J_{C-F}$=30.7 Hz), 129.03, 128.98, 128.39, 125.88 (q, $J_{C-F}$=273.0 Hz), 127.03 (q, $J_{C-F}$=5.7 Hz), 122.29, 109.13, 107.35, 102.98, 74.15 (q, $J_{C-F}$=2.5 Hz), 41.55. HRMS (m/z): calculated for $C_{20}H_{16}F_3N_3O_3$ [M+H]$^+$ 404.1216, found 404.1220.

Example 9

The preparation steps are the same as in Example 1, except that the brominated compound

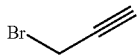

is replaced with

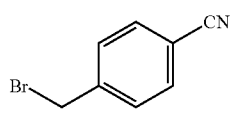

to obtain a compound 1-9, a colorless oil with a yield of 70%. $^1$H NMR (400 MHz, MeOD) δ 7.75-7.68 (m, 2H), 7.63 (s, 1H), 7.52 (d, J=8.0 Hz, 2H), 7.15 (m, 2H), 7.01 (s, 1H), 6.90 (s, 1H), 6.83-6.78 (m, 1H), 5.96 (s, 2H), 5.34 (s, 4H). $^{13}$C NMR (100 MHz, MeOD) δ 154.54, 150.89, 149.70, 149.69, 144.74, 133.41, 129.86, 129.85, 128.41, 128.40, 122.33, 119.60, 112.75, 109.16, 107.34, 103.01, 76.71, 41.66. HRMS (m/z): calculated for $C_{20}H_{16}N_4O_3$ [M+Na]$^+$ 383.1295, found 383.1106.

Comparative Example 1

The preparation steps are the same as in Example 1, except that the brominated compound

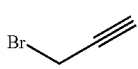

is replaced with

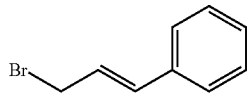

to obtain a compound I-10 having a structure formula represented by formula VIII, a white powder with a yield of 70%. $^1$H NMR (400 MHz, MeOD) δ 7.68 (s, 1H), 7.45-7.39 (m, 2H), 7.34-7.27 (m, 2H), 7.26-7.14 (m, 3H), 7.06 (s, 1H), 6.90 (s, 1H), 6.81 (d, J=8.0 Hz, 1H), 6.67 (d, J=15.9 Hz, 1H), 6.45 (m, 1H), 5.96 (s, 2H), 5.32 (s, 2H), 4.90 (m, 2H). $^{13}$C NMR (100 MHz, MeOD) δ 153.69, 150.70, 149.66, 137.96, 134.98, 129.64, 128.96, 128.91, 128.72, 127.63, 127.62, 125.85, 125.84, 122.16, 109.13, 107.35, 102.94, 76.56, 41.61. HRMS (m/z): calculated for $C_{21}H_{19}N_3O_3$ [M+H]$^+$ 362.1499, found 362.1505.

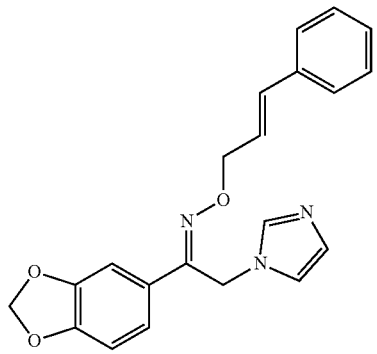

formula VIII

Test Example 1

Using oxiconazole and quercetin as positive controls, the inhibitory effects of the products prepared in Examples 1-9 and Comparative Example 1 on the NO production in lipopolysaccharide-induced BV-2 microglia and the corresponding cell viability were evaluated. The test result is shown in Table 1.

TABLE 1

Test results of the inhibitory effect of the products prepared in Examples 1-9 and Comparative Example 1 on the NO production in lipopolysaccharide-induced BV-2 microglia and the corresponding cell viability

| compound | EC$_{50}$ (μM) | cell viability (%) |
|---|---|---|
| I-1 | 2.07 ± 0.56 | 92.5 |
| I-2 | 5.41 ± 0.22 | 96.1 |
| I-3 | 3.42 ± 0.64 | 97.8 |
| I-4 | 2.12 ± 0.56 | 96.5 |
| I-5 | 2.76 ± 0.34 | 93.3 |
| I-6 | 4.43 ± 0.43 | 97.8 |
| I-7 | 2.37 ± 0.17 | 92.8 |
| I-8 | 2.53 ± 0.47 | 95.4 |
| I-9 | 4.24 ± 1.02 | 91.6 |
| I-10 | >20 | 96.3 |
| oxiconazole | 13.5 ± 0.1 | 96.2 |
| quercetin | 9.56 ± 1.62 | 94.3 |

As shown in Table 1, compared with oxiconazole and quercetin, the (Z)-3,4-methylenedioxyphenylimidazolylethanonexime ether derivatives I-1-I-9 prepared in the examples of the present disclosure show a strong inhibitory effect on the NO production in lipopolysaccharide-induced BV-2 microglia with an $EC_{50}$ value of 2.07-5.41 µmol/L and without significant cytotoxicity (cell viability >90%). However, the compound I-10 prepared in Comparative Example 1 shows a weak inhibitory effect with an $EC_{50}$ value of more than 20 µmol/L.

Test Example 2—Barnes Maze Test

The AD model mice used are 5×FAD transgenic mice, purchased from the Jackson Laboratory (JAX), USA. The transgenic mice have Swedish (K670N/M671L), Florida (I716V) and London (V717I) mutations in amyloid precursor protein (APP), and M146L and L286V mutations in PSEN1.

All mice were fed and watered ad libitum at 22±2° C. with a humidity of 50±10% and a 12 h light/dark cycle until 6 months old, then the experiment was started. All operations were in accordance with the guidelines of the National Health Administration and the guidelines for the use of laboratory animals. The experiment was divided into 6 groups, namely WT-Vehicle group, WT-I-1 low-dose group (the effective concentration of compound I-1 was 15 mg/kg per day), WT-I-1 high-dose group (the effective concentration of compound I-1 was 30 mg/kg per day), 5×FAD-Vehicle group, 5×FAD-I-1 low-dose group (the effective concentration of compound I-1 was 15 mg/kg per day), and 5×FAD-I-1 high-dose group (the effective concentration of compound I-1 was 30 mg/kg per day), among them, the mice used in the WT-Vehicle group, WT-I-1 low-dose group and WT-I-1 high-dose group were wild-type healthy mice, and the mice used in the 5×FAD-Vehicle group, 5×FAD-I-1 low-dose group and 5×FAD-I-1 high-dose group were 5×FAD transgenic mice; the mice in WT-I-1 low-dose group and 5×FAD-I-1 low-dose group were intraperitoneally injected with compound I-1 at a dose of 15 mg/kg/day, the mice in WT-I-1 high-dose group and the 5×FAD-I-1 high-dose group were intraperitoneally injected with compound I-1 at a dose of 30 mg/kg/day, the wild-type healthy mice were given a solvent, and the administration was continuously for 4 weeks. After the administration period, a behavioral test was carried out. Details were referred to the methods of behavioral tests (Barnes maze, Y maze, elevated plus maze, and marble burying test) to evaluate the learning and memory abilities, working memory abilities and anxiety behaviors of mice.

The Barnes maze test is widely used to assess spatial learning and memory abilities. The Barnes maze is a circular platform (92 cm in diameter, 105 cm high from the ground), composed of 20 fixed-distance holes (5 cm in diameter, 38 cm from the center, and 3 cm from the edge of the platform). In the whole experiment, four visual cues of different shapes were continuously placed on a wall of a test room. An escape box (6×12×6 cm) was installed under a fixed hole. On the day before training, the mice were placed in the center of the platform under light to move freely around the platform for 10 s. After 10 s, the mice were gently guided into the escape box, and then the hole was covered with a black polyvinyl alcohol plastic plate for 60 s to allow the mice to adapt to the escape box. During the 4-day training process, the mice were placed in a dimly-lit polyethylene transparent cylinder (11.3 cm in diameter and 15 cm in height) located in the center of the platform. When the cylinder was removed, light was given to allow the mice to explore the platform and find the escape box within 180 s, the time when the mice entered the escape box was recorded by a camera-based EthoVision system (Noldus) and recorded as the escape latency. If the mice did not enter the escape box within 180 s, they were guided into the escape box, and the escape latency was considered to be 180 s. The successful escape latency of mice was recorded and analyzed.

Figure 4:
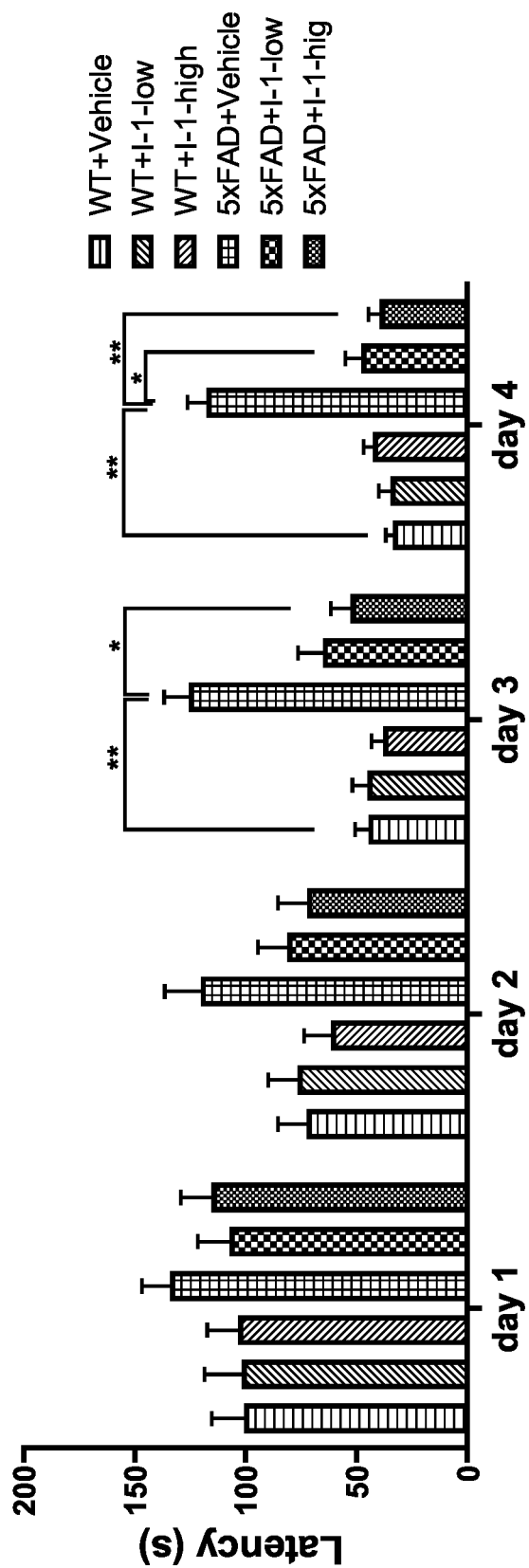
FIG. 4 shows the test results of compound I-1 prepared in Example 1 of the present disclosure on improving the learning and memory ability of 5×FAD mice.

Test Results:

As shown in FIG. 4, on day 3 and day 4, the mice in the 5×FAD-Vehicle group have a significantly higher escape latency compared to the mice in WT-Vehicle group in the Barnes maze test. After the 5×FAD mice are treated with high dose of I-1, the successful escape latency is significantly reduced, and on day 4, after the 5×FAD mice are treated with low dose of I-1, the successful escape latency is also significantly reduced compared to that of the mice in the 5×FAD-Vehicle group, indicating compound I-1 can improve the learning and memory ability of AD model mice.

2. Y Maze Test

The Y maze test is a commonly used test method to assess working memory ability. The Y maze consists of 3 equal arms (40×15×9 cm). The mice were placed in the center of the Y maze to explore the 3 arms freely for 5 min, all movements were recorded by a camera, and the spontaneous alternation ratio was calculated according to the situation of entering onto each arm.

Figure 5:
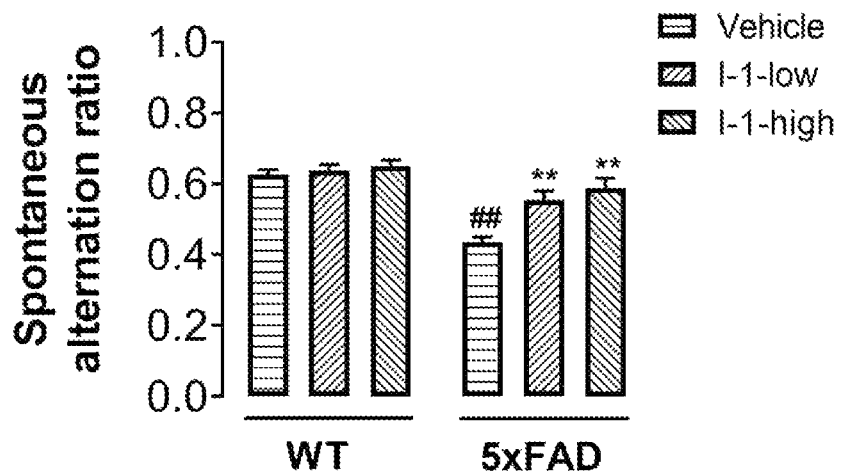
FIG. 5 shows the test results of compound I-1 prepared in Example 1 of the present disclosure on improving the working memory ability of 5×FAD mice.

Test Results:

As shown in FIG. 5, the spontaneous alternation ratio of mice in the 5×FAD-Vehicle group is extremely significantly reduced compared to that of the mice in the WT-Vehicle group in the Y maze test. After the mice in 5×FAD group are treated with low dose of I-1 and high dose of I-1, the spontaneous alternation ratio is significantly increased, indicating that compound I-1 can improve the working memory ability of AD model mice.

3. Elevated Plus Maze Test

The elevated plus maze is a recognized behavior test used for anxiety behavior assessment. The elevated plus maze consists of 4 arms with a length of 30 cm, a width of 6 cm, and a height of 40 cm from the ground. There are high walls with a height of 15 cm on two "closed" arms, and there are protrusions with a height of 1 mm on the edges of the other two "open" arms (without walls) to prevent falling. The mice were gently placed in the central area (8×8 cm) where the four arms crossed, and were allowed to freely explore for 5 min. The times of entries onto the open arm and the total times were recorded, and the anxiety behavior of the animal was evaluated by the proportion of entries onto the open arm.

4. Marble Burying Test

Each mouse was placed in a cage (28×18×12 cm) containing 20 clean marbles (1.5 cm in diameter), evenly distributed on the surface of clean wood chips (4 cm in depth). After 30 min, each mouse was removed from the cage and the number of marbles buried at least two-thirds was counted.

Test Results:

In order to evaluate the psychological and behavioral changes of AD mice, the elevated plus maze test and the marble burying test were used in the study. As shown in panel A of FIG. 6, an elevated plus maze was used to assess the anxiety level of 5×FAD mice. The results show that the proportion of entries onto the open arm in 5×FAD-Vehicle group is significantly reduced compared to that of the WT-Vehicle group, after the 5×FAD mice are treated with low dose of I-1 and high dose of I-1, the proportion of entries onto the open arm is significantly improved, indicating that compound I-1 can alleviate the anxiety behavior of AD model mice. Marble burying behavior is a manifestation of anxiety and compulsive behaviors instinctively in rodents.

Figure 6:
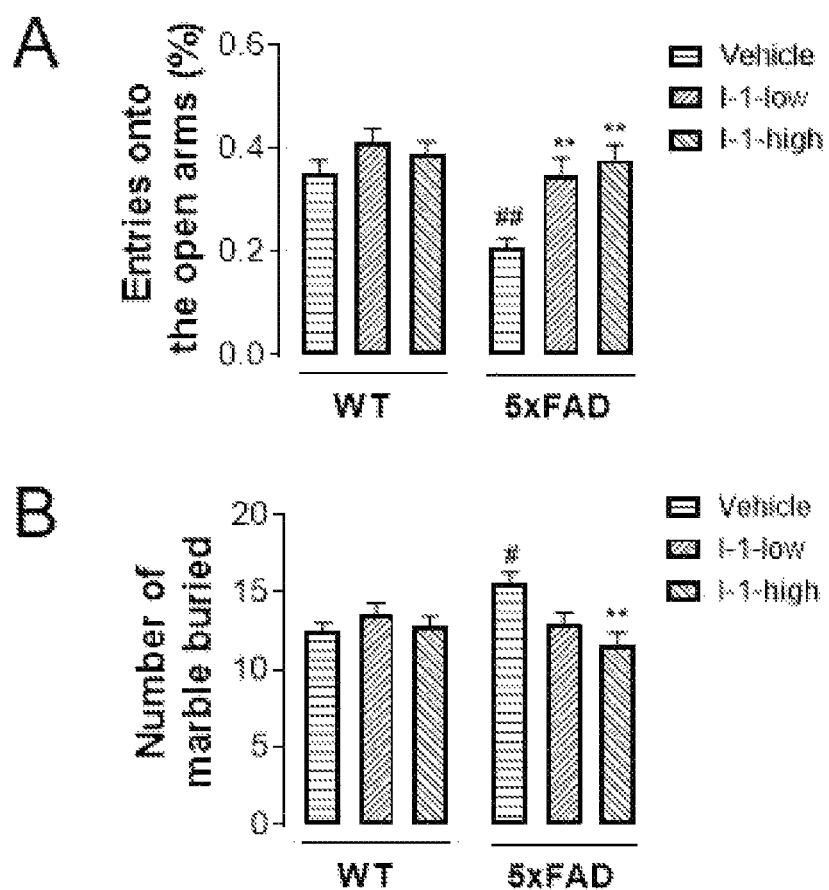
FIG. 6 shows the test results of compound I-1 prepared in Example 1 of the present disclosure on alleviating anxiety behavior of 5×FAD mice.

As shown in panel B of FIG. 6, the number of marbles buried by mice in the 5×FAD-Vehicle group is significant increased compared to that of the WT-Vehicle group, suggesting that AD model mice have obvious anxiety-like behaviors. After the 5×FAD mice are treated with high dose of I-1, the number of marbles buried is significantly reduced, indicating that compound I-1 can alleviate the anxiety behavior of AD model mice.

Although the above embodiments give a detailed description of the present disclosure, they are only a part of the embodiments of the present disclosure, rather than all of the embodiments. People can also obtain other embodiments based on the embodiment without any creativity. These embodiments all belong to the protection scope of the present disclosure.

What is claimed is:

1. A (Z)-3,4-methylenedioxyphenylimidazolylethanonexime ether derivative having a structure represented by formula I:

formula I

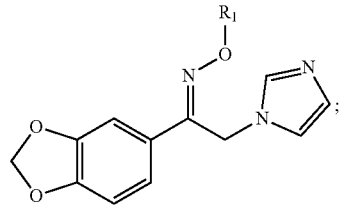

wherein, $R_1$ is one of a $C_3$-$C_5$ alkene group, a $C_3$-$C_5$ alkynyl group, a benzyl group and a substituted benzyl group; and the substituted benzyl group is a haloalkyl substituted benzyl group and/or a cyano substituted benzyl group.

2. The (Z)-3,4-methylenedioxyphenylimidazolylethanonexime ether derivative according to claim 1, wherein having any one of the structures represented by formula I-1-I-9:

I-1

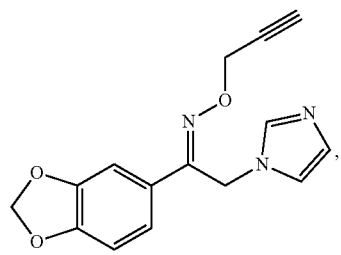

I-2

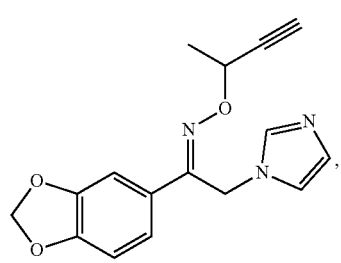

I-3

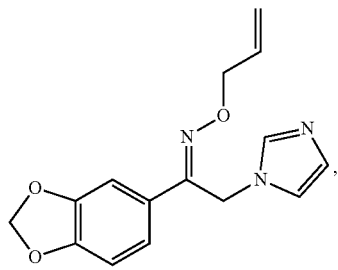

I-4

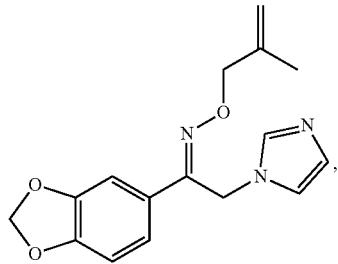

I-5

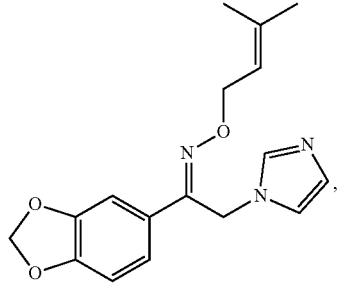

I-6

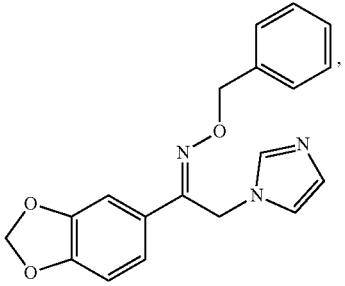

I-7

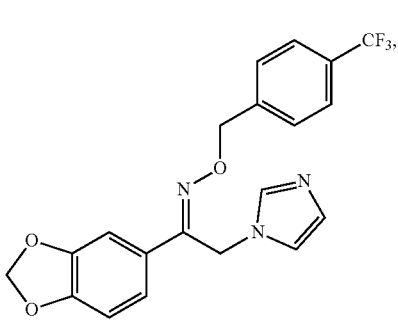

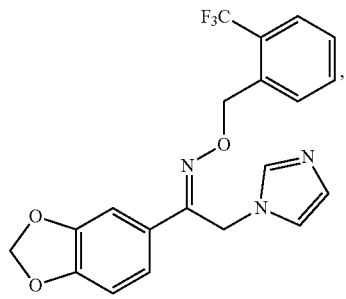

I-8

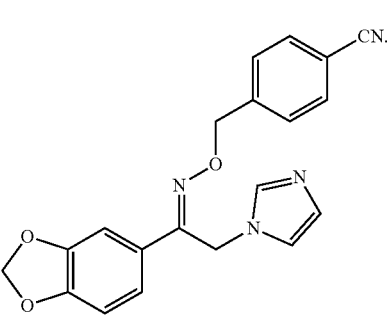

I-9

3. A method for preparing the (Z)-3,4-methylenedioxyphenylimidazolylethanonexime ether derivatives according to claim 1, comprising steps of:
mixing and subjecting 1-(benzo[d][1,3]dioxol-5-yl)-2-(1H-imidazol-1-yl)ethan-1-one oxime, an alkali metal hydride, a halogenated compound and an organic solvent to a nucleophilic substitution reaction to obtain the (Z)-3,4-methylenedioxyphenylimidazolylethanonexime ether derivatives;
the halogenated compound is selected from the group consisting of a $C_3$-$C_5$ halogenated olefin, a $C_3$-$C_5$ halogenated alkyne, a benzyl halide, and a substituted benzyl halide; and the substituted benzyl halide is an alkyl substituted benzyl halide and/or a cyano substituted benzyl halide.

4. The method according to claim 3, wherein a method for preparing 1-(benzo[d][1,3]dioxol-5-yl)-2-(1H-imidazol-1-yl)ethan-1-one oxime includes steps of:
mixing and subjecting 1-(benzo[d][1,3]dioxol-5-yl)-2-(1H-imidazol-1-yl)ethan one, an alkali metal salt of an organic acid, hydroxylamine hydrochloride, a water scavenger and an organic solvent to an imidization reaction to obtain the 1-(benzo[d][1,3]dioxol-5-yl)-2-(1H-imidazol-1-yl)ethan-1-one oxime.

5. The method according to claim 4, wherein a method for preparing 1-(benzo[d][1,3]dioxol-5-yl)-2-(1H-imidazol-1-yl)ethan-1-one includes steps of:
mixing and subjecting 2-halo-1-(benzo[d][1,3]dioxol-5-yl)ethan-1-one, 1H-imidazole, an inorganic weak base and an organic solvent to a N-alkylation reaction to obtain 1-(benzo[d][1,3]dioxol-5-yl)-2-(1H-imidazol-1-yl)ethan-1-one.

6. The method according to claim 3, wherein a mass ratio of 1-(benzo[d][1,3]dioxol-5-yl)-2-(1H-imidazol-1-yl)ethan-1-one oxime, the halogenated compound and the alkali metal hydride is 2: (0.75-1.2): 0.2.

7. The method according to claim 4, wherein a mass ratio of 1-(benzo[d][1,3]dioxol-5-yl)-2-(1H-imidazol-1-yl)ethan-1-one, the alkali metal salt of an organic acid and the water scavenger is 2: (1.5-1.6): 1, and a mass ratio of 1-(benzo[d][1,3]dioxin-5-yl)-2-(1H-imidazol-1-yl)ethan-1-one and hydroxylamine hydrochloride is 2: (1.3-1.4);
a holding temperature of the imidization reaction is 70-95° C.; a holding time of the imidization reaction is 12-15 h; and the imidization reaction is carried out under heating and refluxing.

8. A composition for the treatment of Alzheimer's disease comprising a (Z)-3,4-methylenedioxyphenylimidazolylethanonexime ether derivative and a pharmaceutically acceptable excipient, the (Z)-3,4-methylenedioxyphenylimidazolylethanonexime ether derivative is the (Z)-3,4-methylenedioxyphenylimidazolylethanonexime ether derivative according to claim 1.

9. The composition for the treatment of Alzheimer's disease according to claim 8, wherein having any one of the structures represented by formula I-1-I-9:

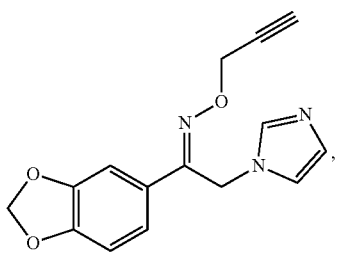

I-1

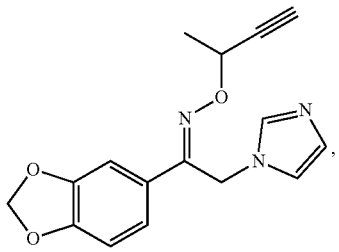

I-2

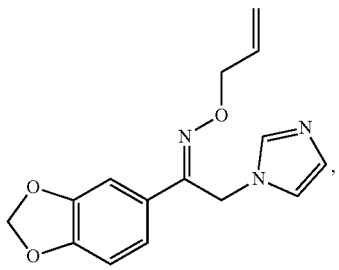

I-3

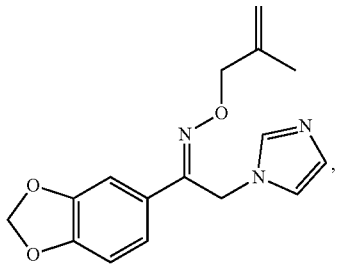

I-4

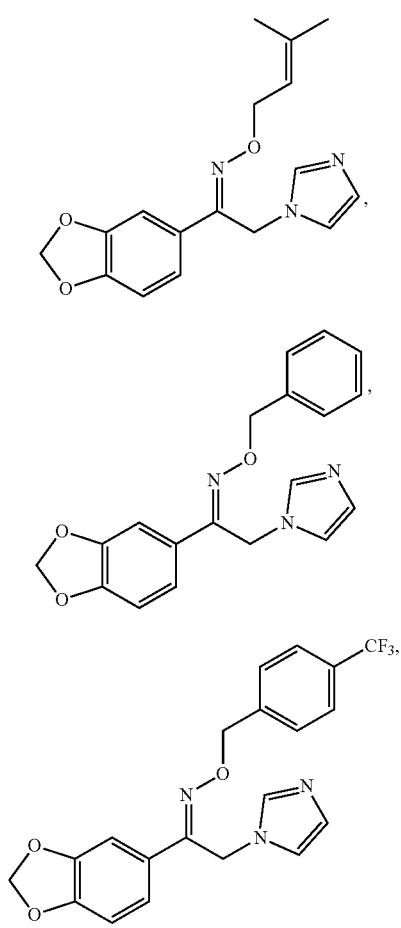
I-5
I-6
I-7
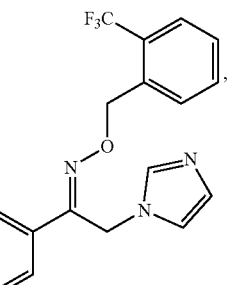
I-8
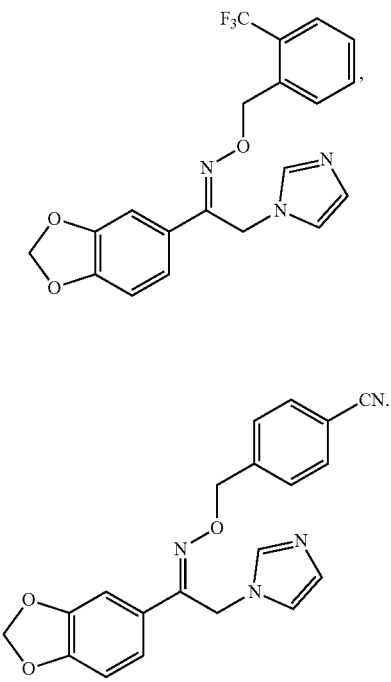
I-9
10. The composition for the treatment of Alzheimer's disease according to claim 8, wherein a dosage form of the composition comprises an injection.
11. The composition for the treatment of Alzheimer's disease according to claim 9, wherein a dosage form of the composition comprises an injection.
* * * * *